United States Patent [19]

Ueda

[11] Patent Number: 4,617,914

[45] Date of Patent: Oct. 21, 1986

[54] END CURVING DEVICE FOR ENDOSCOPE

[75] Inventor: Hirohisa Ueda, Tokyo, Japan

[73] Assignee: Asahi Kogaku Kogyo Kabushiki Kaisha, Tokyo, Japan

[21] Appl. No.: 743,730

[22] Filed: Jun. 12, 1985

[51] Int. Cl.[4] .............................................. A61B 1/00
[52] U.S. Cl. ...................................................... 128/4
[58] Field of Search ................................ 128/4, 5, 6, 7

[56] References Cited

U.S. PATENT DOCUMENTS

| 4,203,430 | 5/1980 | Takahashi | 128/4 |
| 4,207,873 | 6/1980 | Krvy | 128/6 |
| 4,461,282 | 7/1984 | Ouchi et al. | 128/4 |
| 4,483,326 | 11/1984 | Yamaka et al. | 128/4 |

Primary Examiner—William H. Grieb
Attorney, Agent, or Firm—Sughrue, Mion, Zinn, Macpeak, and Seas

[57] ABSTRACT

An end curving device for an endoscope of a type having a pair of wires connected at one end to a curving end portion of the endoscope adapted to be inserted into a body cavity, and an operating lever in an operating section which pushes and pulls the wires upon manual activation by the operator. An internal gear is formed on the shaft of the operating lever and is rotatably supported in the operating section. First and second pinions, which are made integral with one another, are engaged with respective racks to which the wires are coupled. The first pinion is engaged with the internal gear.

9 Claims, 7 Drawing Figures

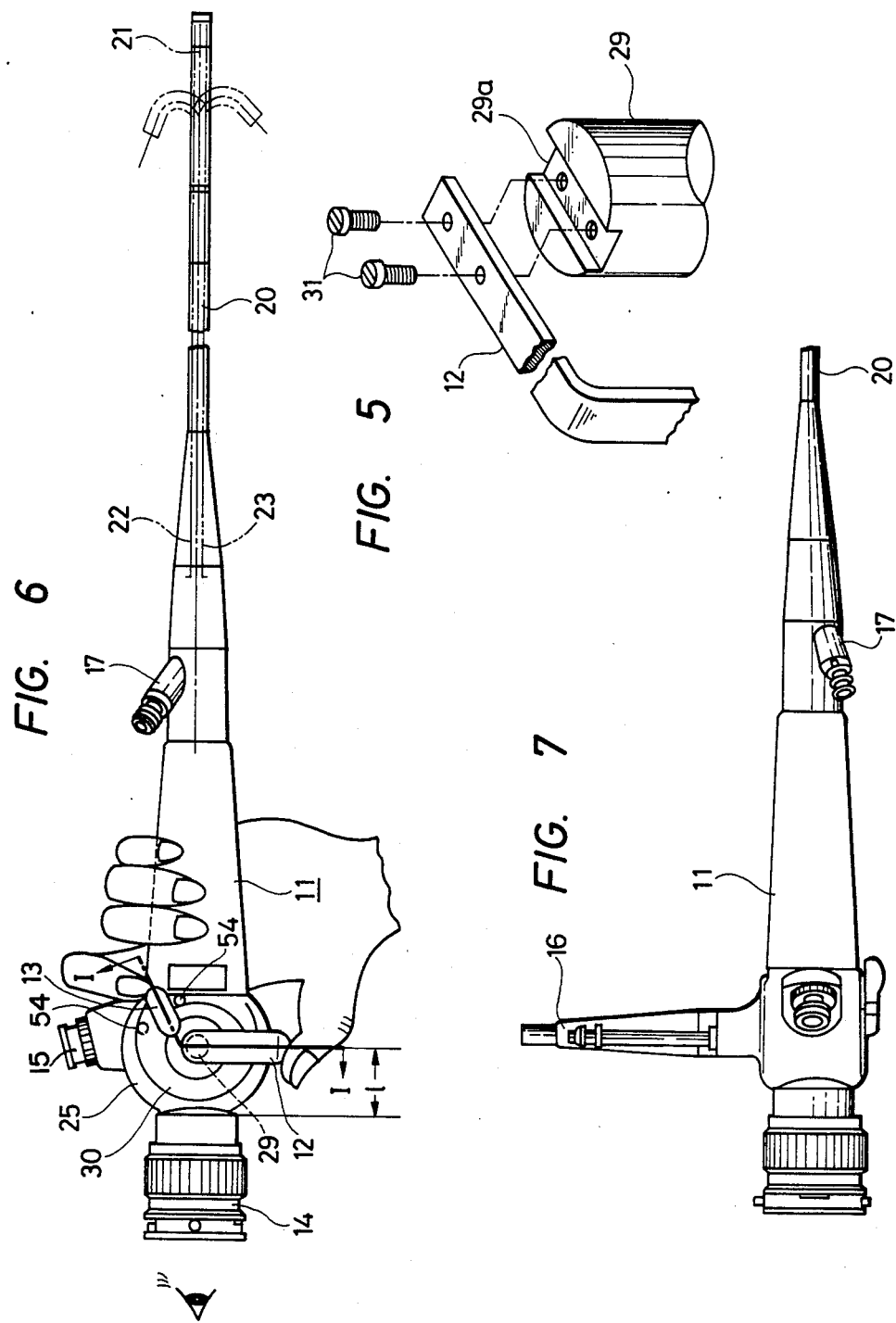

END CURVING DEVICE FOR ENDOSCOPE

BACKGROUND OF THE INVENTION

The present invention relates to an end curving device for controlling the bending of the curving section of an endoscope with an operating section which is manually operable by the operator.

In an end curve device for an endoscope, one or two pairs of operating wires coupled to the curving section provided at the end of the endoscope are coupled at their opposite ends to the operating section, and the curving section is bent in a desired direction by pulling one of the operating wires while pushing the other.

Available operating wire driving devices can be generally classified into a first group in which the operating wires are wound on a pulley and the pulley is turned by operating an operating lever, and a second group in which the operating wires are driven through a rack-and-pinion mechanism. In the former group, the construction is relatively simple. However, in order to increase the amount of movement of the operating wires per unit angle of rotation of the pulley, it is necessary to increase the diameter of the pulley, and therefore the operating section is necessarily bulky. Furthermore, since the operating wires are wound on a pulley, the operating wires are repeatedly bent and rubbed by the pulley, leading to relatively frequent breakage of the wires. On the other hand, in the latter group in which a rack-and-pinion mechanism is employed, a pair of racks coupled to a pair of operating wires are engaged with a single pinion, and the pinion is operated to drive the operating wires. If the pinion were to be driven directly with the operating lever, then similarly as in the above-described first group, in order to increase the amount of movement of each operating wire per unit angle of rotation, it would be necessary to increase the diameter of the pinion. Furthermore, since the racks extend beyond the pinion, the operating section is larger in size than that of the first group employing a pulley. The speed of the device may be increased by arranging intermediate gears between the pinion and the racks. However, in such a mechanism, the direction of rotation of the pinion is opposite to the directions of movement of the racks. Therefore, the operating wires must be crossed with each other between the operating section and the curving section at the end of the device. However, crossing the operating wires results in excessively large forces being applied to the operating wires. As a result, the operating wires are liable to be fatigued, worn, and broken.

SUMMARY OF THE INVENTION

An object of the invention is thus to provide an end curving device for an endoscope in which the above-described difficulties accompanying a conventional end curving device have been eliminated and the amount of movement of each operating wire per angle of rotation of an operating lever is large although the overall size of the device is relatively small, and in which it is unnecessary to cross the operating wires.

Another object of the invention is to provide an end curving device for an endoscope in which the amount of movement of each operating wire per angle of rotation of an operating lever can be readily adjusted.

In accordance with the above and other objects, in an end curving device for an endoscope according to the invention, an internal gear is integrally formed on an operating lever which is rotatably held in an operating section, and a second pinion engaged with the internal gear is provided in such a manner that it is integral with a first pinion, the latter being engaged with a pair of racks to which are coupled a pair of operating wires.

In this device, the intermediate gear is interposed between the operating lever and the first pinion engaged with the racks. However, the direction of rotation of the operating lever coincides with the directions of movement of the racks, and accordingly it is unnecessary to cross the operating wires. Furthermore, the amount of movement of each operating wire per angle of rotation of the operating lever can be relatively freely determined by adjusting the number of teeth of the intermediate gear. Accordingly, the operating section can be miniaturized.

BRIEF DESCRIPTION OF THE DRAWINGS

FIG. 5 is an exploded perspective view showing essential components of an example of the connection of an operating lever shaft and an operating lever;

FIG. 6 is a front view showing the external appearance of an endoscope incorporating the end curving device according to the invention; and FIG. 7 is a plan view of the same.

DESCRIPTION OF THE PREFERRED EMBODIMENTS

Figure 1:
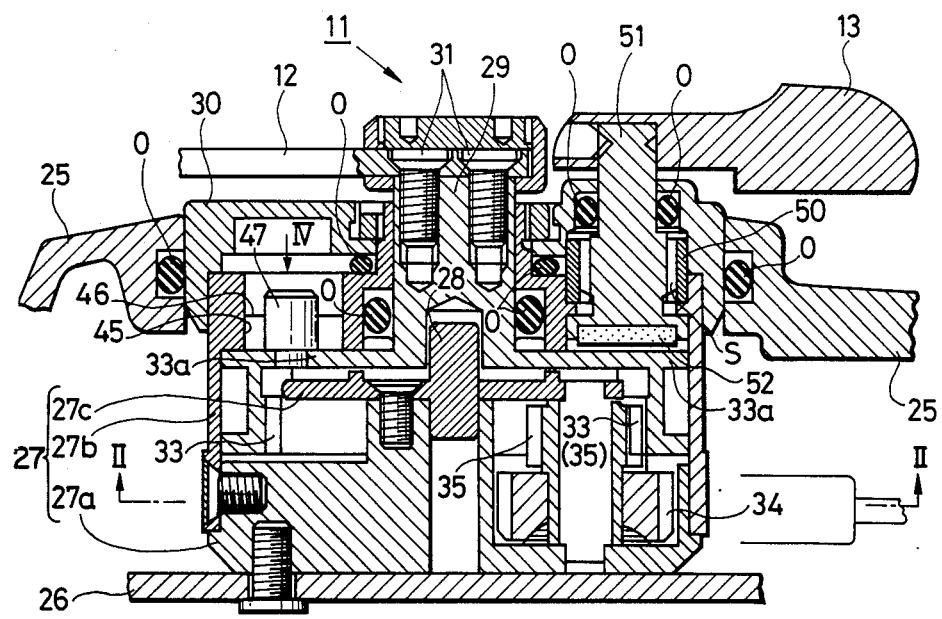
FIG. 1 is a sectional view taken along a line I—I in FIG. 6 showing an example of an end curving device for an endoscope according to the invention.

The invention will be described with reference to preferred embodiments shown in the accompanying drawings.

FIGS. 6 and 7 show an endoscope incorporating an end curving device according to the invention. An operating section 11 includes an operating lever 12, a stopping lever 13, an eyepiece 14, and other well-known components such as a suction valve 15, a light guide cable 16, and an extractor inlet 17. The operating lever 12 is substantially L shaped. As shown in FIG. 6, the operator's thumb is placed on a part of the operating lever 12 which has a thumb receiving portion and which extends below the operating section 11.

The operating section 11 is connected to the rear end of an inserting section 20 which is flexible and is adapted to be inserted into the body. The front end of the inserting section 20 is connected to a curving section 21. The curving section 21 is made up of a number of articulated elements connected with pins, and it is connected to operating wires 22 and 23, indicated by chain lines in FIG. 6. When the operating lever 12 is operated to pull or push the operating wires 22 and 23, the curving section 21 is curved vertically or horizontally, as indicated by chain lines in FIG. 6. An image observing optical fiber bundle, an illuminating optical fiber bundle, and an extractor channel (not shown) are inserted into the inserting section 20 and the curving section 21. The image observing optical fiber bundle has a front end confronting an objective lens provided at the end of the curving section 21 and a rear end confronting the eyepiece section 14. The illuminating optical fiber bundle has a front end confronting an illuminating window at the end of the curving section and a rear end lead to the light guide cable 16. The extractor channel is used to cause the extractor inserted through the extractor inlet 17 to protrude from the end of the curving section 21.

Figure 3:
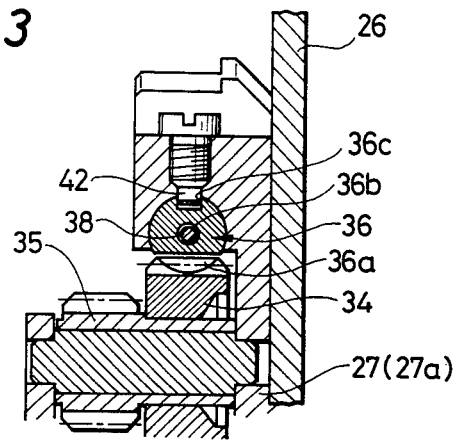
FIG. 3 is a sectional view taken along a line III—III in FIG. 2.
Figure 4:
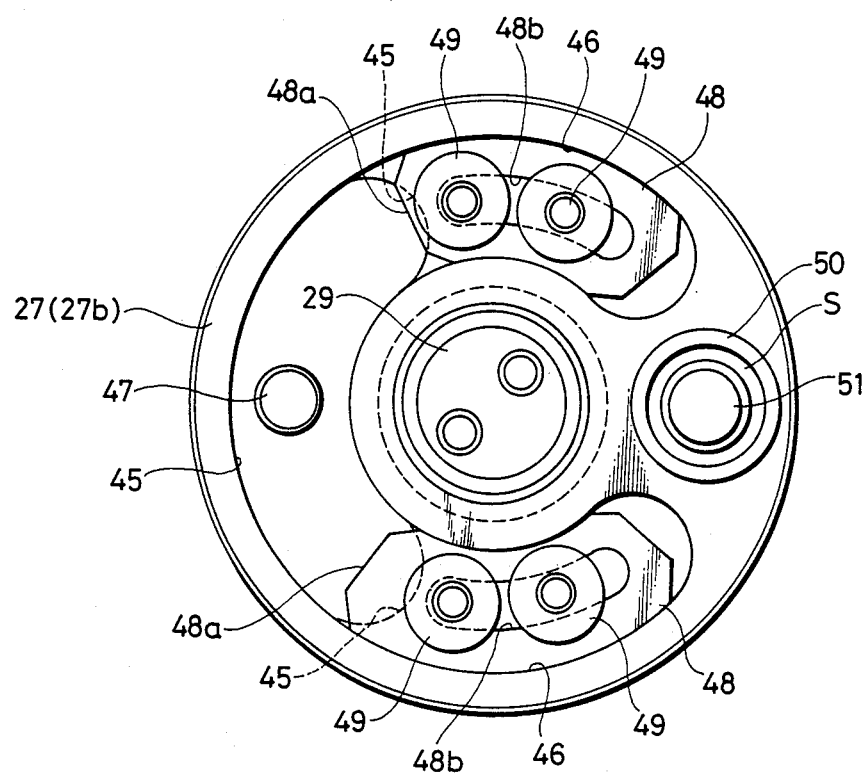
FIG. 4 is a diagram, viewed in the direction of an arrow IV in FIG. 1, showing the device from which a gear cover has been removed.

As shown in FIGS. 1 and 3, a main plate 26 is fixedly provided in the casing 25 of the operating section 11, and a gear case 27 is fixedly secured to the main plate 26. The gear case 27 is composed of an inner case 27a, an outer case 27b, and a pinion supporting plate 27c. An operating lever shaft 29 is rotatably mounted on a central shaft 28 attached to the pinion supporting plate 27c. The operating lever shaft 29 extends through the gear case 27 and a gear cover 30, and protrudes from the casing 25. As shown in FIG. 5, a diametrical groove 29a is formed in the end face of the protruding operating lever shaft 29. The operating lever 12 is shrink-fitted into the groove 29a, and is then secured to the latter with screws 31. It is also possible for a groove to be formed in the operating lever 12 and a protrusion formed on the end face of the operating lever shaft 29 and the protrusion shrink-fitted into the groove thus formed. In this case, even if the operating lever 12 is pushed forwardly or rearwardly with a strong force, the operating lever 12 and the operating lever shaft 29 are held tightly fixed to each other at all times. The junction portions of the operating lever 12 and the operating lever shaft 29 are covered with decorative covers 18a and 18b (FIG. 1).

Inside the gear case 27, the operating lever shaft 29 has an internal gear 33 formed integrally thereon. The internal gear 33 is held between the pinion supporting plate 27c and the outer case 27b by a disk part 33a provided behind the gear 33 and mounted in such a manner that it cannot come off. A first pinion 34 and a second pinion 35, which are made integral with one another, are rotatably supported by the pinion supporting plate 27c and the inner case 27a. The second pinion 35 is engaged with the internal gear 33.

Figure 2:
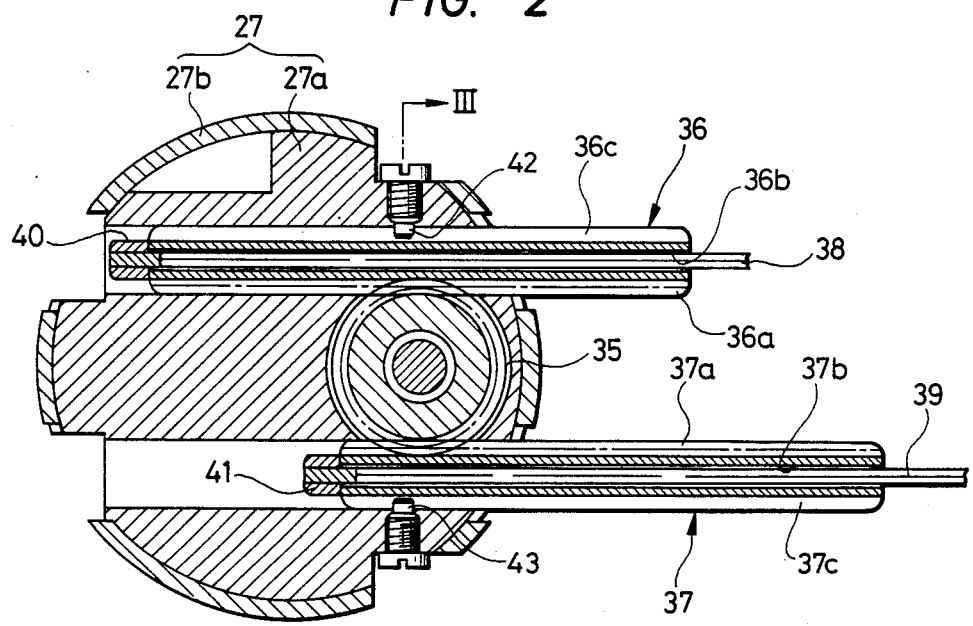
FIG. 2 is a sectional view taken along a line II—II in FIG. 1.

As is apparent from FIGS. 2 and 3, racks 36a and 37a, formed on respective rack bars 36 and 37, are engaged with the first pinion 34 symmetrically with respect to the center of the latter. Operating power transmitting bars 38 and 39 are loosely inserted into axial holes 36b and 37b in the rack bars 36 and 37, respectively. Retaining blocks 40 and 41 are fixedly secured to the rear ends of the operating power transmitting bars 38 and 39, respectively. The front ends of the bars 38 and 39 are connected to the rear ends of the operating wires 22 and 23, respectively. Straight advance guide grooves 36c and 37c are formed in the sides of the rack bars 36 and 37 which are opposite to those in which the racks 36a and 37a are formed. Guide pins 42 and 43 secured fixedly to the gear case 27 are engaged with the grooves 36c and 37c, respectively, whereby the rack bars 36 and 37 are guided in their longitudinal direction of movement.

When the operating lever shaft 29 is turned with the operating lever 12, the internal gear 33 is rotated. The rotation of the gear 33 is transmitted to the second pinion 35 and the first pinion 34. As a result, the rack bars 36 and 37, being engaged with the first pinion, are moved in opposite directions so that the operating wires 22 and 23 are also moved in opposite directions through the operating power transmitting bars 38 and 39, thus bending the curving section 21. In this bending operation, the pulled rack bar 36 (or 37) moves the operating power transmitting bar 38 (or 39) via the retaining block 40 (or 41), while the pushed (extended) rack bar 37 (or 36) is not moved together with the operating power transmitting bar 39 (or 38) because the bars 38 and 39 are only loosely inserted into the axial holes 36b and 37b. This protects the operating wires 22 and 23 from being forcibly returned, and thus prevents the operating wires from being deformed, fatigued, or broken. In the above-described embodiment, since the first pinion 34 is positioned in front of the operating lever shaft 29, space for allowing the rack bars 36 and 37 to move rearwardly is readily available. Accordingly, it is possible to miniaturize the operating section 11 by reducing the distance l (FIG. 6) between the operating lever shaft 29 and the eyepiece section 14.

Next, a mechanism for controlling the range of rotation of the operating lever 12 will be described. A circumferentially elongated through-hole 45 and stepped holes 46 are formed in the outer case 27b of the gear case 27 with the stepped holes 46 being located on both sides of the through-hole 45. A stopper pin 47, fixed to the disk part 33a provided behind the internal gear 33, extends through the through-hole 45. An arcuate stopper plate 48 having a stopper surface 48a at one end of the through-hole 45 is fitted in each of the stopped holes 46 in such a manner that it is movable circumferentially. A position adjusting hole 48b is formed in the central part of each stopper plate 48. Screws 49 pass through the position adjusting holes 48b and are engaged with the outer case 27b. The stopper plates 48 can be freely moved by loosening the screws 49. As the operating lever 12 is turned, the stopper pin 47 is turned through the operating lever shaft 29 and the disk part 33a; however, the stopper pin 47 is limited in rotation by the stopper surfaces 48a of the stopper plates 48. More specifically, the positions of the stopper surfaces 48a and 48a are determined by adjusting the positions of the stopper plates 48, whereby the angle of rotation of the operating lever 12, i.e., the maximum amount of curving of the curving section, is determined. The positions of the stopper plates 48 are adjusted with the gear cover removed.

The curving section 21 can be curved by turning the operating lever 12 as described above. In order to maintain the curving section 21 curved, it is necessary to provide a braking mechanism for preventing rotation of the operating lever 12. In the braking mechanism of the invention, the rotation of the internal gear 33 is controlled. Specifically, a threaded ring 50 is fixedly secured to the outer case 27b of the gear case 27 located outside of the operating lever shaft 29. A brake shaft 51 is threadably engaged with the threaded ring 50 by means of threads S. A brake pad 52 made of a cork plate or synthetic resin plate is fixed to the lower end face of the brake shaft 51 in position confronting the disk part 33a of the internal gear 33. The outer end portion of the brake shaft 51 protrudes from the gear cover 30 and is fixedly engaged with the stopping lever 13.

With the arrangement, as the brake shaft 51 is turned with the stopping lever 13, the brake pad 52 can be moved into or out of engagement with the disk part 33a of the internal gear 33. When the brake pad 52 is strongly pushed against the disk part 33a, the rotation of the internal gear 33 is stopped, and accordingly the curve imparted to the curving section 21 is held.

As shown in FIG. 6, the stopping lever 13 is positioned obliquely above the operating lever shaft 29, which contributes to an improvement in the operability of the endoscope (which is usually operated with the left hand). Assuming that the brake pad is engaged with the disk part when the stopping lever 13 is swung downwardly in FIG. 6 and the brake pad is disengaged from the disk part when the stopping lever 13 is swung upwardly, the left hand can grip the operating section 11 and the thumb can operate the operating lever 12 to bend the curving section 21. When the curving section 21 is suitably bent, the stopping lever 13 is swung downwardly with the index finger. Under this condition, the curve given to the curving section is held, even if the thumb is released from the operating lever 12. The curving section can be released by pushing the stopping lever 13 upwardly with the thumb. Thus, the operator can readily operate the operating lever 12 and the stopping lever 13 without moving his eye from the eyepiece section 14.

A rotation-range regulating member is provided for the stopping lever also so that an excessively strong force cannot be applied to push the brake pad 52 against the disk part 33a of the internal gear 33 and to prevent the brake shaft 51 from coming off the threaded ring 50.

Further, the rotation-range regulating member may be arranged such that, as in the rotation-range regulating mechanism for the operating lever 12, the position is adjustable, or it may utilize a stopper 54 (FIG. 6) which protrudes from the gear cover 30.

The endoscope is made watertight so that it can be easily sterilized after use. In FIG. 1, reference character 0 designates several 0-rings inserted between various components.

As is apparent from the above description, in the end curving device of the endoscope according to the invention, an internal gear is integrally formed on an operating lever shaft which is rotatably held in an operating section, and a second pinion engaged with the internal gear is provided integrally with a first pinion, the latter being engaged with racks coupled to the operating wires. Therefore, the amount of movement of the racks with respect to the angle of rotation of the operating lever shaft can be freely determined by choice of the numbers of teeth of the internal gear, the first pinion, and the second pinion. The device of the invention can be applied to a variety of endoscopes merely by changing these gear members. Accordingly, the number of common components is increased, which contributes to a reduction of manufacturing cost. The center of the internal gear is shifted from the center of the first and second pinions. However, the amount of shift is much smaller than that what it would be if the second pinion were engaged with the external gear, and accordingly the operating section can be made small in size. Since the center of the internal gear is shifted from the center of the pinions as described above, with respect to the center of the internal gear, the first and second pinions can be moved towards the inserting section. Accordingly, the space needed for the racks to move backwardly of the first and second pinions is readily obtained, with the result that the operating section is well balanced with the distance between the operating lever shaft and the eyepiece section reduced. Furthermore, because the device of the invention employs the internal gear, completely the same as in the case where a pinion integral with the operating lever shaft is engaged directly with a pair of racks, the direction of rotation of the operating lever and the desired direction of movement of the racks is achieved without having to cross the operating wires. Accordingly, the difficulties whereby the wires are excessively bent and accordingly fatigued and possibly broken are eliminated.

I claim:

1. An end curving device for an endoscope in which at least one pair of operating wires are connected to a curving section provided at a front end of an inserting section adapted to be inserted into a human body, and an operating lever in an operating section is operated to push and pull said pair of operating wires to curve said curving section, wherein the improvement comprises:
   an internal gear integrally formed on a shaft of said operating lever and rotatably supported in said operating section;
   a first pinion;
   a pair of racks coupled to respective ones of said pair of operating wires and engaged with said first pinion; and
   a second pinion integral with said first pinion and engaged with said internal gear.

2. The end curving device for an endoscope of claim 1, wherein said shaft of said operating lever has a disk part joining said internal gear and a central part of said shaft.

3. The end curving device for an endoscope of claim 2, further comprising a gear case having a pinion supporting plate, an inner case, and an outer case, said internal gear extending at least partially between said pinion supporting plate and said inner case so as to be held thereby.

4. The end curving device for an endoscope of claim 3, further comprising a pinion shaft fixed to said pinion supporting plate for rotatably supporting said first and second pinions.

5. The end curving device for an endoscope of claim 1, further comprising means for establishing an angular range of rotation of said operating lever shaft.

6. The end curving device for an endoscope of claim 2, wherein said angular range establishing means comprises: a stopper pin fixed to said disk part, and at least one adjustable plate for stopping movement of said stopper pin at an adjustable position.

7. The end curving device for an endoscope of claim 2, further comprising means for selectively braking and holding a desired rotary position of said operating lever shaft.

8. The end curving device for an endoscope of claim 7, wherein said braking and holding means comprises: a braking lever; a brake shaft fixed to said braking lever, said brake shaft having a threaded portion threadedly engaged with a fixed member; and a disk pad fixed to an end of said brake shaft adjacent a surface of said disk part, whereby, upon rotation of said brake lever in a predetermined direction, said disk pad is brought into engagement with said disk part to stop rotation of said disk part.

9. The end curving device for an endoscope of claim 1, wherein said wires pass loosely through longitudinal passages formed in respective ones of said racks, and further comprising a retaining block at the end of each of said wires adjacent said racks.

* * * * *